United States Patent
Lee

(10) Patent No.: US 9,715,243 B2
(45) Date of Patent: *Jul. 25, 2017

(54) TIMING CONTROLLED AC TO DC CONVERTER AND METHOD

(71) Applicant: ALFRED E MANN FOUNDATION FOR SCIENTIFIC RESEARCH, Santa Clarita, CA (US)

(72) Inventor: Edward K. F. Lee, Fullerton, CA (US)

(73) Assignee: ALFRED E. MANN FOUNDATION FOR SCIENTIFIC RESEARCH, Santa Clarita, CA (US)

( * ) Notice: Subject to any disclaimer, the term of this patent is extended or adjusted under 35 U.S.C. 154(b) by 216 days.

This patent is subject to a terminal disclaimer.

(21) Appl. No.: 14/599,779

(22) Filed: Jan. 19, 2015

(65) Prior Publication Data

US 2015/0130435 A1 May 14, 2015

Related U.S. Application Data

(63) Continuation of application No. 12/963,598, filed on Dec. 8, 2010, now Pat. No. 8,937,825.

(60) Provisional application No. 61/285,520, filed on Dec. 10, 2009.

(51) Int. Cl.
  *H02M 7/217* (2006.01)
  *G05F 1/56* (2006.01)
  *G05F 1/59* (2006.01)
  *H02M 3/158* (2006.01)
  *H02M 7/219* (2006.01)

(52) U.S. Cl.
  CPC ............ *G05F 1/56* (2013.01); *G05F 1/59* (2013.01); *H02M 3/158* (2013.01); *H02M 7/217* (2013.01); *A61B 2560/0219* (2013.01); *H02M 2007/2195* (2013.01); *Y02B 70/1408* (2013.01)

(58) Field of Classification Search
  CPC ....................................................... H02M 7/217
  USPC ............................................................ 363/89
  See application file for complete search history.

(56) References Cited

U.S. PATENT DOCUMENTS

| | | | | |
|---|---|---|---|---|
| 6,657,417 B1* | 12/2003 | Hwang | ..................... | G05F 1/70 323/207 |
| 2005/0046405 A1* | 3/2005 | Trafton | ..................... | G05F 1/56 323/308 |
| 2008/0224681 A1* | 9/2008 | Padure | ................. | H02M 3/1588 323/288 |
| 2009/0146634 A1* | 6/2009 | Audy | ..................... | H02M 3/156 323/290 |
| 2010/0327836 A1* | 12/2010 | Li | ....................... | H02M 3/1588 323/283 |

\* cited by examiner

*Primary Examiner* — Jue Zhang
*Assistant Examiner* — Trinh Dang
(74) *Attorney, Agent, or Firm* — Malcolm J. Romano

(57) ABSTRACT

A timing controlled converter and method for converting a time varying input signal to a regulated DC output voltage for application to a load circuit. A feedback loop is employed as a control means for switchably coupling the time varying input signal to the load circuit for controlled periods of time in a manner so as to provide an average load voltage equal to a reference voltage. The duration of the controlled periods of time is a function of: the difference between the time varying input signal and the output voltage; and the integral of the difference between the output voltage and the reference voltage.

6 Claims, 7 Drawing Sheets

TIMING CONTROLLED AC TO DC CONVERTER AND METHOD

CROSS REFERENCE TO RELATED APPLICATIONS

The present application is a continuation of U.S. patent application Ser. No. 12/963,598 filed on Dec. 8, 2010, which issued on Jan. 20, 2015 as U.S. Pat. No. 8,937,825 and claims the benefit under 35 U.S.C. §119(e) to U.S. Provisional Application No. 61/285,520, filed on Dec. 10, 2009, both of which are incorporated herein by reference in their entirety.

FIELD OF THE INVENTION

This disclosure relates generally to electronic integrated circuits for use typically in implantable biomedical devices. More specifically, the disclosure relates to a timing controlled AC to DC converter.

BACKGROUND OF THE INVENTION

Many biomedical implantable devices are powered from an external time varying magnetic source. The magnetic source is inductively coupled to a coil housed within the implantable device to induce an AC voltage in the coil which is then converted or rectified to a regulated DC voltage for use to power device electronics. As a general matter, higher supply voltages are often required for analog circuits, such as stimulation circuits in implantable neuro-prosthetic devices, whereas lower supply voltages are usually required for digital circuits and processors. Accordingly, a rectified or regulated DC voltage is typically maintained at a higher value for analog circuits and a linear regulator is implemented to convert the higher value DC voltage to a lower supply voltage for the digital circuits. An example of an implantable stimulator that includes both analog and digital circuitry and voltage supplies providing a range of output voltages is found in U.S. Pat. No. 6,185,452 to Schulman, et al. As has been recognized, the approach taken in the art to generate multiple supply voltages as described above, is not very power efficient especially when considering the limited power availability from weak inductive coupling of the implanted device with the external time varying magnetic source. Attempts have been made to improve power efficiency such as the use of Buck converters and switchable capacitor converters; however they may not be suitable for neuro-prosthetic and biomedical implant applications due to the limited space available within the devices which typically can only accommodate a few discrete components. Accordingly, what is needed to satisfy the shortcomings of the prior art is an approach based on a direct conversion of the induced AC voltage to a regulated DC voltage which achieves high conversion efficiency using circuitry sufficiently small to be housed in small implantable devices.

SUMMARY

An example embodiment of the invention discloses a timing controlled AC to DC converter which supplies a regulated output voltage to a load circuit. The converter switchably couples a time varying input signal for a controlled period of time directly to the load circuit in a manner such that the average value of the regulated output voltage equals a preselected reference voltage. An embodiment of the invention comprises an integrator arranged to integrate the difference between the output or load voltage and the preselected reference voltage to thereby generate a threshold or control signal. A switch is arranged to switchably couple the time varying input signal to the load circuit for controlled periods of time. A controlled period of time commences when the time varying input signal becomes greater than the output voltage and terminates when the time varying input signal becomes greater than the value of the control signal. The duration of the controlled periods of time, so defined, causes the converter to provide an average value of the output voltage being equal to the preselected reference voltage while minimizing power loss and significantly improving converter efficiency.

BRIEF DESCRIPTION OF DRAWINGS

The accompanying drawings, which are incorporated into and constitute a part of this specification, illustrate one or more embodiments of the present disclosure, and together with the description of example embodiments, serve to explain the principles and implementations of the disclosure.

FIG. 1A shows an implementation of a power management unit using a switched-capacitor (SC) converter; FIG. 1B shows an implementation of a power management unit using a buck converter; and FIG. 1C shows an implementation of a power management unit using a linear regulator.

DETAILED DESCRIPTION

Figure 1A:
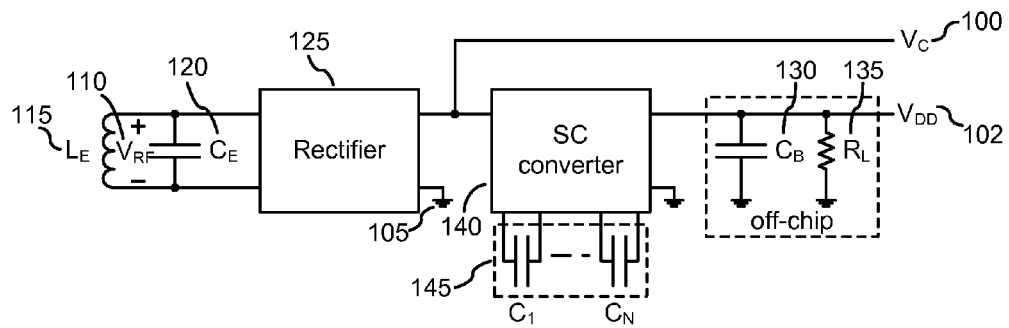
FIGS. 1A-1C show circuit implementations of conventional power management units known in the art. More particularly.
Figure 1B:
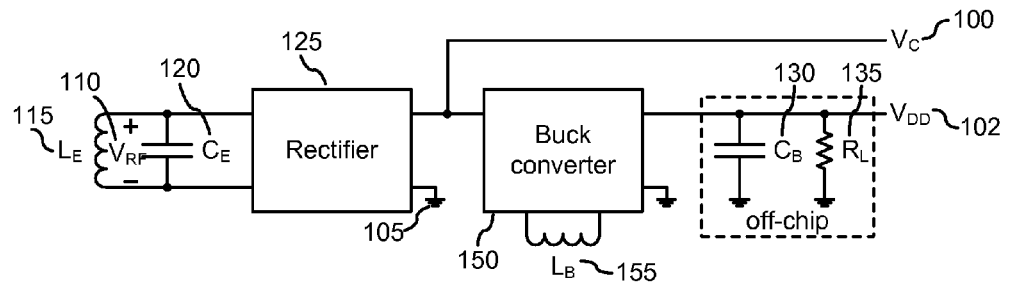
Figure 1C:
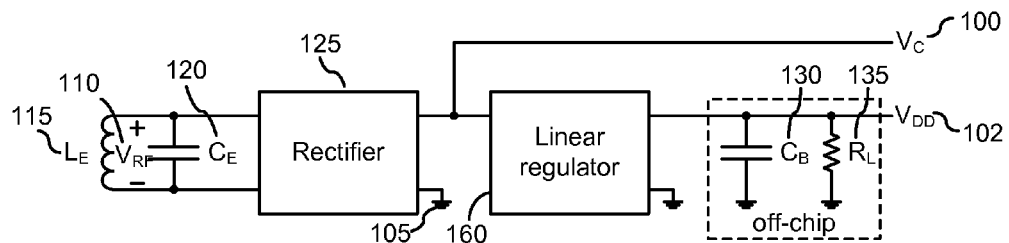

Power management units or voltage converter circuits housed within implantable medical devices are generally used to generate supply voltages required for operation of electronic circuits within the devices. As an illustration, FIGS. 1A-1C show conventional implementations of power management units housed within implantable devices. Power management units typically generate a high voltage supply $V_C$ (100), which may be used by a stimulator to generate stimulation current pulses and a low output voltage $V_{DD}$ (102), which may be used for powering various low voltage circuits. According to several embodiments of the present invention, converter circuits are assumed to receive power through inductive coupling from a radio frequency (RF) magnetic field, which is the case for many implantable biomedical devices. A metric used to characterize the converter is power efficiency, denoted as $\eta$. Power efficiency $\eta$ is defined as a ratio between the output power of the converter to the input power supplied to the converter. Consequently, a high power efficiency η signifies that a large proportion of the input power is available as output power, which is generally desired.

Specifically, according to several embodiments of the present invention converters in implantable biomedical devices are powered from an external time varying magnetic source (not shown). The external magnetic source is magnetically coupled to a coil $L_E$ (115). This magnetic coupling results in an induced voltage $V_{RF}$ (110) across the coil $L_E$ (115). A tuning capacitor $C_E$ (120) is designed to resonate at an operating frequency $f_{in}$. A conventional rectifier (125) is used to generate the high supply voltage $V_C$ (100) measured between Vc and ground (105). The high supply voltage $V_C$ (100) derives from the positive peak value and a negative peak value of the induced voltage $V_{RF}$ (110).

In the present disclosure, the induced voltage $V_{RF}$ (110) across the coil $L_E$ (115) is assumed to be periodic and has a peak value higher than the required high supply voltage $V_C$ (100). In particular, the induced voltage $V_{RF}$ (110) is arbitrarily assumed to be a sinusoidal wave. Consequently, after rectifying the induced voltage $V_{RF}$ (110), the rectifier (125) can produce the high supply voltage $V_C$ (100) equal to or less than the peak voltage of the induced voltage $V_{RF}$ (110).

The low supply voltage $V_{DD}$ (102), on the other hand, can be generated by taking the high supply voltage $V_C$ (100) of the rectifier (125) and converting it to a desired value for the low supply voltage $V_{DD}$ (102). Specifically, DC to DC converters, such as switched-capacitor converters, buck converters, and linear regulators, may be used to generate the low supply voltage $V_{DD}$ (102).

As seen from FIGS. 1A-1C (and later in FIG. 2), the coil $L_E$ (115), tuning capacitor $C_E$ (120), and rectifier (125) are common to the different implementations of the converters. Additionally, the induced voltage $V_{RF}$ (110), high supply voltage $V_C$ (100), and low supply voltage $V_{DD}$ (102) refer to the same voltages in each of FIGS. 1A-1C. Since the components (115, 120, 125) and the voltages (110, 100, 102) referred to are the same for different implementations of converter units, the same reference numerals are used to refer to the same components (115, 120, 125) and voltages (110, 100, 102) in each of FIGS. 1A-1C. Additionally, a load circuit, which is not part of the converter unit, comprises a bypass capacitor $C_B$ (130) and a load resistor $R_L$ (135). The bypass capacitor $C_B$ (130) is used to remove any AC voltage components from the low supply voltage $V_{DD}$ (102) such that only a DC voltage component is applied to the load resistor $R_L$ (135). The same off-chip load circuit will be used in many subsequent figures.

FIG. 1A shows an implementation that utilizes a switched-capacitor (SC) converter (140) for generating the low supply voltage $V_{DD}$ (102). The SC converter (140) can achieve high power efficiency η. However, the SC converter (140) requires a plurality of discrete capacitors (145) comprising $C_1$ through $C_N$.

The number of discrete capacitors (145) in a typical design, denoted as N, is approximately given by the equation $N=V_C/V_{DD}-1$. Consequently, for a typical high supply voltage $V_C$ (100) of 10 V to 15 V and typical low supply voltage $V_{DD}$ (102) of 3 V, the number N of discrete capacitors (145) ranges from 2 to 4. This number N does not include the bypass capacitor $C_B$ (130).

FIG. 1B shows an implementation that utilizes a buck converter (150) for generating the low supply voltage $V_{DD}$ (102). The number of discrete components is reduced in this implementation because of using a buck converter. However, the disadvantage of this implementation is the necessity for the inclusion of an inductor $L_B$ (155).

FIG. 1C shows an implementation of a converter unit that utilizes a linear regulator (160) for generating the low supply voltage $V_{DD}$ (102). This implementation that utilizes the linear regulator (160) does not require extra discrete components aside from the bypass capacitor $C_B$ (130). However, current flowing to the load resistor $R_L$ (135) also flows through the linear regulator (160). As a result, an equivalent power of $(V_C-V_{DD})\cdot V_{DD}/R_L$ is dissipated by the linear regulator (160) for a total power consumption of $V_C\cdot V_{DD}/R_L$ drawn from the high supply voltage $V_C$ (100).

With continued reference to FIG. 1C, for a value of 3V for the low output voltage $V_{DD}$ (102) and a range of 10V to 15V for the large output voltage $V_C$ (100), power efficiency η is between 20% and 30%, which is not very efficient. Although the implementations using the SC converter (140) and the buck converter (150) generally have higher power efficiencies compared to the implementation using linear regulators, especially for high load conditions, the implementation of the converter unit using the linear regulator (160), shown in FIG. 1C, is often the only viable choice for implantable devices due to their small size.

Figure 2:
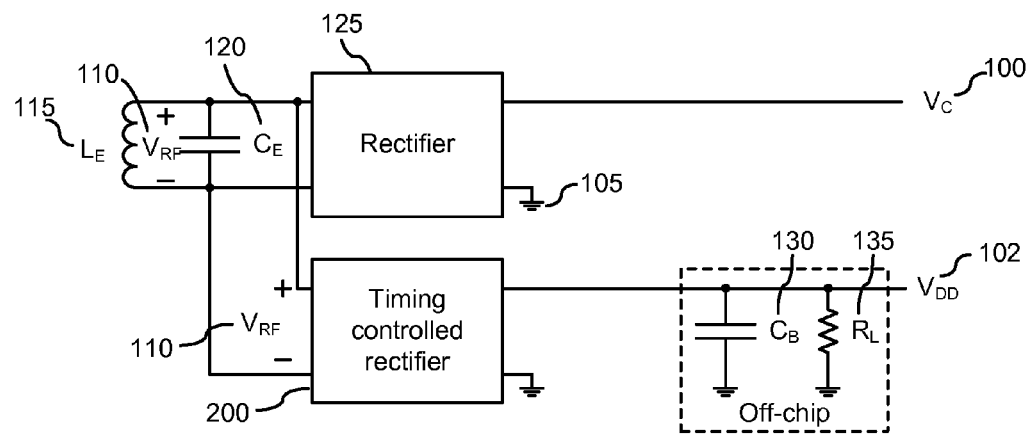
FIG. 2 shows an implementation of a timing controlled converter in accordance with an embodiment of the present invention.

FIG. 2 shows an implementation of an AC to DC converter of the present invention using a timing controlled rectifier (200), henceforth referred to as TCR. By comparing FIG. 2 with FIGS. 1A-1C, the coil $L_E$ (115), tuning capacitor $C_E$ (120), and rectifier (125) are common to the different implementations. The induced voltage $V_{RF}$ (110), high supply voltage $V_C$ (100), and low supply voltage $V_{DD}$ (102) in FIG. 2 refer to the same voltages in each of FIGS. 1A-1C. The low supply voltage $V_{DD}$ (102) may be considered the output voltage of the AC to DC converter circuit of the present invention. Additionally, the same off-chip load circuit comprising the bypass capacitor $C_B$ (130) and the load resistor (135) is also used in FIG. 2.

The TCR (200) is adapted to generate the output voltage $V_{DD}$ (102) directly from the induced voltage $V_{RF}$ (110). The TCR (200) can achieve relatively good power efficiency without using extra discrete components aside from the bypass capacitor $C_B$ (130).

The induced voltage $V_{RF}$ (110) is directly applied to the rectifier (125) and to the TCR (200). The TCR (200) converts the induced voltage $V_{RF}$ (110), which is an AC signal, into the required output voltage $V_{DD}$ (102), which is a DC voltage. The rectifier (125) is used to generate the high supply voltage $V_C$ (100) by rectifying the positive peak value and negative peak values of the induced voltage $V_{RF}$ (110).

Figure 3:
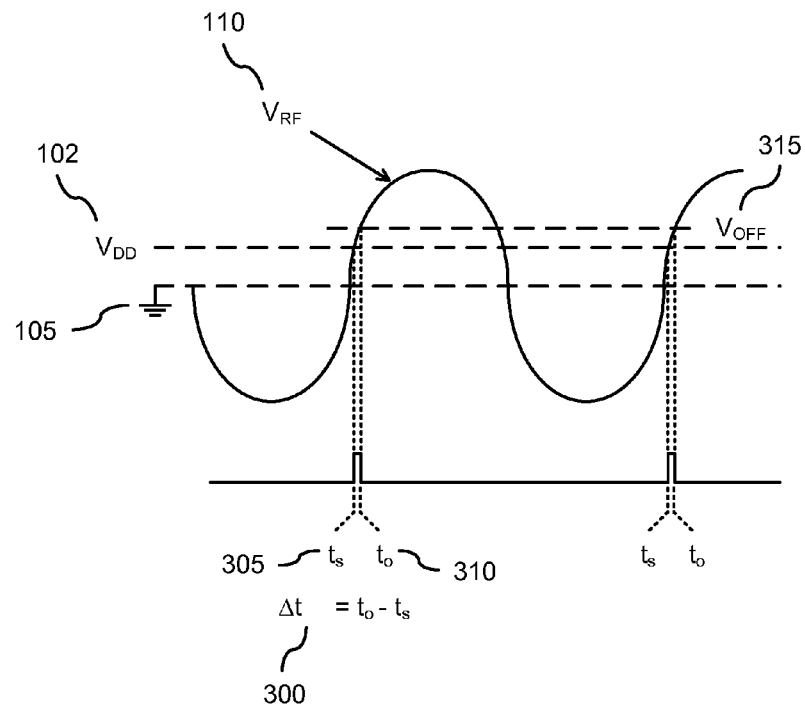
FIG. 3 shows a voltage waveform that illustrates the controlled period of time during which the converter couples the time varying input signal to the load circuit.

FIG. 3 shows an exemplary voltage waveform for the induced voltage $V_{RF}$ (110) and also illustrates the method of setting the controlled period of time for coupling $V_{RF}$ (110) to a load circuit, which in this case comprises bypass capacitor $C_B$ (130) and load resistor $R_L$ (135) and which also defines the basic operation of the TCR (200). As illustrated in FIG. 3, the controlled amount of time for coupling $V_{RF}$ (110) to a load circuit is shown by a turn-on period Δt (300).

The TCR's (200) turn-on period Δt (300) occurs for a time period where the induced voltage $V_{RF}$ (110) is slightly above the output voltage $V_{DD}$ (102), as illustrated in FIG. 3. In particular, the TCR's (200) turn-on period Δt (300) is given as a difference between a turn-on time $t_s$ (305) and a turn-off time $t_o$ (310). During the turn-on period Δt (300), the TCR (200) conducts current from the voltage source $V_{RF}$ (110) to the load circuit (capacitor $C_B$ (130) and load resistor $R_L$ (135)) otherwise identified as output voltage $V_{DD}$ (102) such that the current is drawn from $V_{RF}$ (110) and stored as accumulated charge in the bypass capacitor $C_B$ (130). The turn-on time $t_s$ (305) and the turn-off time $t_o$ (310) will be described in more detail in relation to FIGS. 4 and 5, in which the operation of the TCR (200) will be described in more detail.

Figure 4:
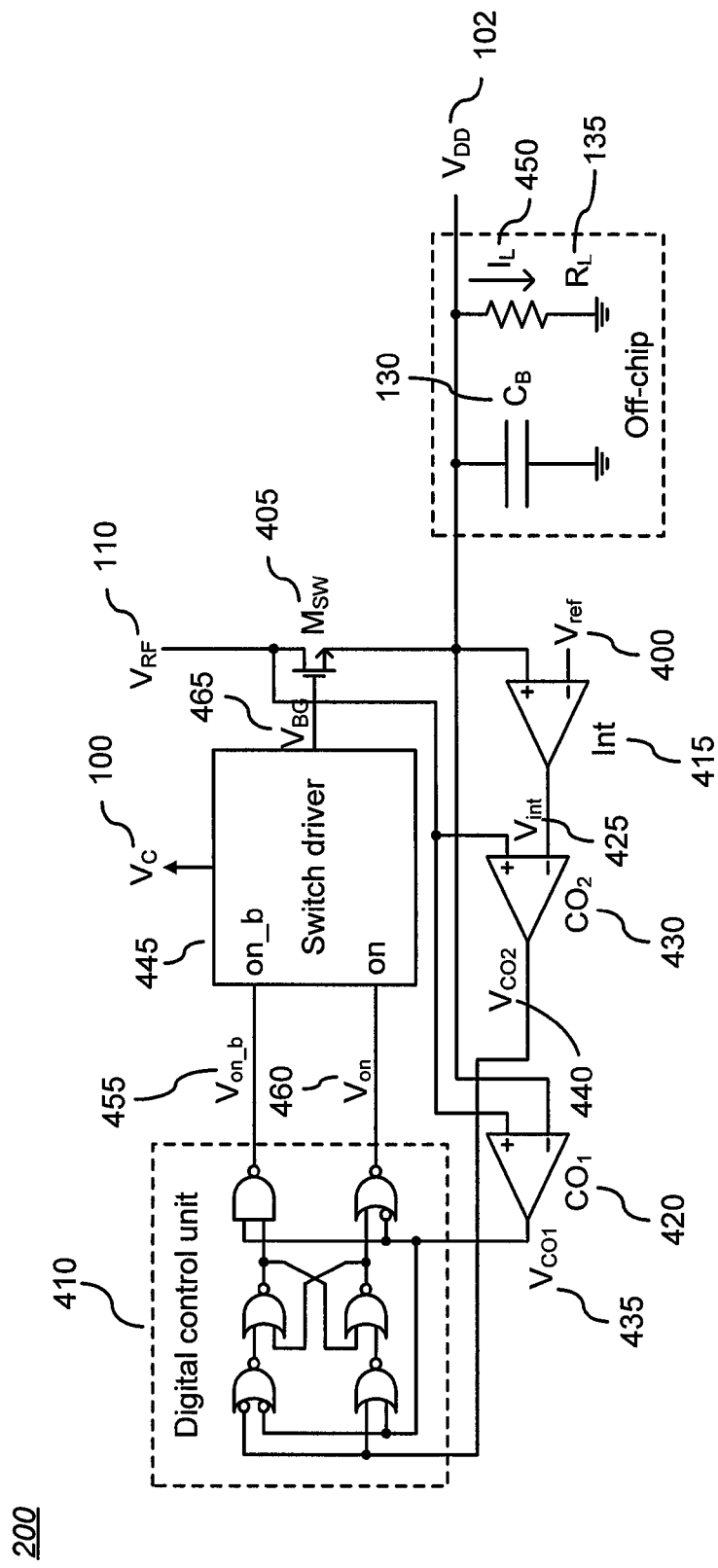
FIG. 4 shows a block diagram of an embodiment of the timing controlled converter of the present invention.

FIG. 4 shows an exemplary embodiment of the TCR (200). The same off-chip components, which comprise the bypass capacitor $C_B$ (130) and load resistor $R_L$ (135), as shown in FIG. 2 are also shown in FIG. 4. As shown in FIG. 4, the value of the output voltage $V_{DD}$ (102) is set by a negative feedback control loop (hereinafter referred to as a "feedback loop") that switchably controls the operation of transistor $M_{SW}$ (405). Specifically, the feedback loop comprises a digital control unit (410), an integrator (415), a first comparator (420), a second comparator (430), a switch driver (445), and the transistor $M_{SW}$ (405).

As a whole, the feedback loop is used to ensure that the transistor $M_{SW}$ (405) turns on only during the portion of time that the induced voltage $V_{RF}$ (110) is increasing in value. Specifically, with reference to the waveform on FIG. 3, the transistor $M_{SW}$ (405) turns on only during the turn-on period $\Delta t$ (300). When the induced voltage $V_{RF}$ (110) becomes larger than the output voltage $V_{DD}$ (102), the transistor $M_{SW}$ (405) will turn on at the time $t_s$ (305).

Specifically, the digital control unit (410), which comprises a specific arrangement of logic gates, takes a first comparator output $V_{CO1}$ (435) and a second comparator outputs $V_{CO2}$ (440) as its inputs and provides a first control voltage $V_{on\_b}$ (455) and a second control voltage $V_{on}$ (460) as its outputs. Both $V_{on\_b}$ (455) and $V_{on}$ (460) are applied as inputs to the switch driver (445). The switch driver (445) provides a switch driver voltage $V_{BG}$ (465), which is applied to the gate of the transistor $M_{SW}$ (405). Logic gates in the digital control unit (410) are designed in such a way as to ensure that transistor $M_{SW}$ (405) turns on only during a portion of time that the induced voltage $V_{RF}$ (110) is increasing in value.

The integrator (415) takes as its input the output voltage $V_{DD}$ (102) and a reference voltage $V_{ref}$ (400). The integrator (415) integrates the difference between the output voltage $V_{DD}$ (102) and the reference voltage $V_{ref}$ (400) and provides thereby a resultant integrated value identified as the integrator output voltage $V_{int}$ (425). The voltage $V_{int}$ (425) is used as a threshold voltage or control signal for application to the second comparator $CO_2$ (430).

The first comparator $CO_1$ (420) has as its inputs the induced voltage $V_{RF}$ (110) and the output voltage $V_{DD}$ (102). The first comparator $CO_1$ (420) detects when the induced voltage $V_{RF}$ (110) becomes larger than the output voltage $V_{DD}$ (102). When the induced voltage $V_{RF}$ (110) becomes larger than the output voltage $V_{DD}$ (102), the first comparator output voltage $V_{CO1}$ (435) output from the first comparator $CO_1$ (420) will cause transistor $M_{SW}$ (405) to turn on at the turn-on time $t_s$ (305). More specifically, the voltage $M_{CO1}$ (435) is applied to the digital control unit (410), which outputs a first output $V_{on\_b}$ (455) and a second output $V_{on}$ (460) to the switch driver (445). The switch driver (445) provides a switch driver output $V_{BG}$ (465) to the gate of the transistor $M_{SW}$ (405), which turns on the transistor $M_{SW}$ (405). When the transistor $M_{SW}$ (405) is turned on, a load current $I_L$ (445) is supplied from $V_{RF}$ (110) to the load resistor $R_L$ (135).

The second comparator $CO_2$ (430) has as its inputs the voltage $V_{RF}$ (110) and the integrator output voltage $V_{int}$ (425). The second comparator $CO_2$ (430) detects when the voltage $V_{RF}$ (110) becomes greater than the integrator output voltage $V_{int}$ (425). When $V_{RF}$ (110) becomes greater than the voltage $V_{int}$ (425), output voltage $V_{CO2}$ (440) of the second comparator $CO_2$ (430) will cause transistor $M_{SW}$ (405) to turn off at the turn-off time $t_o$ (310). The truth table (Table 1) shown below illustrates the relationship between the identified voltages and the corresponding state of transistor $M_{SW}$ (405).

TABLE 1

| Voltage | Condition | $V_{BG1}$ | Transistor $M_{SW}$ |
| --- | --- | --- | --- |
| $V_{CO1}$ | High if $V_{RFa} > V_{DD}$ | High | ON |
| | Low if $V_{RFa} < V_{DD}$ | Low | OFF |
| $V_{CO2}$ | High if $V_{RFa} > V_{int}$ | High | OFF |
| | Low if $V_{RFa} < V_{int}$ | Low | ON |

For the TCR (200) shown in FIG. 4, a load current $I_L$ (450) flows from voltage source $V_{RF}$ (110) to the load circuit. Operation of the feedback loop, and thus operation of the TCR (200) itself, is as follows. When the average load current $I_L$ (450) increases, the average output voltage $V_{DD}$ (102) decreases. Since the integrator output voltage $V_{int}$ (415) is a function of the difference between the voltages $V_{DD}$ (102) and $V_{ref}$ (400), the integrator output voltage $V_{int}$ (415) increases when $V_{DD}$ (102) decreases. Since the first comparator output $V_{CO1}$ (435) is a function of the difference between the voltages $V_{RF}$ (110) and $V_{DD}$ (102), the first comparator $CO_1$ (420) will have a logic high at the output earlier when the voltage $V_{DD}$ (102) decreases, which causes transistor $M_{SW}$ (405) to turn on earlier. Since the second comparator output $V_{CO2}$ (440) is a function of the difference between the voltages $V_{RF}$ (110) and $V_{int}$ (415), the second comparator $CO_2$ (430) will have a logic high at the output later when the voltage $V_{int}$ (415) increases, which would cause transistor $M_{SW}$ (405) to turn off later. Hence, the turn-on period $\Delta t$ (300) for the transistor $M_{SW}$ (405) will become longer and more charge will be accumulated in the bypass capacitor $C_B$ (130).

Steady state is reached when an average value of the output voltage $V_{DD}$ (102) becomes equal to the reference voltage $V_{ref}$ (400). In the steady state, voltage $V_{int}$ (425) will become nearly constant and the transistor $M_{SW}$ (405) will turn on and off for an amount of time needed to accumulate just enough charge to keep the average value of the output voltage $V_{DD}$ (102) equal to the reference voltage $V_{ref}$ (400). As a result, the average value for the output voltage $V_{DD}$ (102) is regulated to have a value equal to the reference voltage $V_{ref}$ (400).

With reference to FIG. 4 and later to FIG. 6, it should be noted that transistor $M_{SW}$ (405) and $M_{SW1}$ (563) in the case of FIG. 6, will be turned on when the polarity of $V_{RF}$ and $V_{DD}$ (535) are the same. Furthermore, it should also be noted that although FIG. 3 and FIG. 6, for example, show and describe $V_{DD}$ as having a positive polarity, the invention contemplates a configuration for operation with $V_{DD}$ having a negative potential with respect to ground. Thus in order to avoid any confusion regarding comparing voltages when referring to relative magnitudes with respect to the use of the terms "greater than", "larger than", "exceeds", and the like, it is to be understood that absolute values of voltage magnitudes are to be considered.

It should be noted that due to any delays attributable to the comparators $CO_1$ (420) and $CO_2$ (430), the voltage $V_{RF}$ (110) at the turn off time $t_o$ (305), denoted as a voltage $V_{OFF}$ (315) in FIG. 3, may be slightly higher than the voltage $V_{int}$ (425). However, the feedback loop will adjust the turn-off time $t_o$ (305) so as to maintain the average value of the output voltage $V_{DD}$ (102) equal to the reference voltage $V_{ref}$ (400).

Consider an ideal case where the transistor $M_{SW}$ (405) has a turn-on resistance $R_{SW}$ (not shown) that is nearly zero and where the comparator (420, 430) delays are zero. The turn-on period $\Delta t$ (300) required to accumulate sufficient charge on the bypass capacitor $C_B$ (130) will approach zero. In this ideal case, the voltage $V_{OFF}$ (315) will equal the output voltage $V_{DD}$ (102). Additionally, in this ideal case, no power is dissipated by the transistor $M_{SW}$ (405) and the power efficiency $\eta$ for converting power from the induced voltage $V_{RF}$ (110) to the output voltage $V_{DD}$ (102) will approach 100%.

As is recognized, transistor $M_{SW}$ (405) has a finite turn-on resistance $R_{SW}$, especially when a high-voltage MOSFET is used for the transistor $M_{SW}$ (405). In such cases, the power efficiency $\eta$ may be about 50% to 90% depending on the frequency and the amplitude of the induced voltage $V_{RF}$ (110), the value of $V_{DD}$, the turn-on period $\Delta t$ and the resistance of the transistor $M_{SW}$. As the frequency of the induced voltage $V_{RF}$ (110) increases, the power efficiency $\eta$ decreases due to higher dynamic power dissipation in driving $M_{SW}$ more frequently. Compared to the implementation utilizing the linear regulator (160) as shown in FIG. 1C, it can be shown that in a case where $V_D > V_{DD}/\eta$, the embodiment of the converter using TCR (200) will provide some power savings by a percentage of $[1-V_{DD}/(\eta V_C)]$ compared to the use of the linear regulator (160). For instance, given an exemplary situation where $V_C=10$ V, $V_{DD}=3$ V and $\eta=50\%$, the TCR (200) will provide a power saving of 40% compared to the use of the linear regulator (160).

Figure 5:
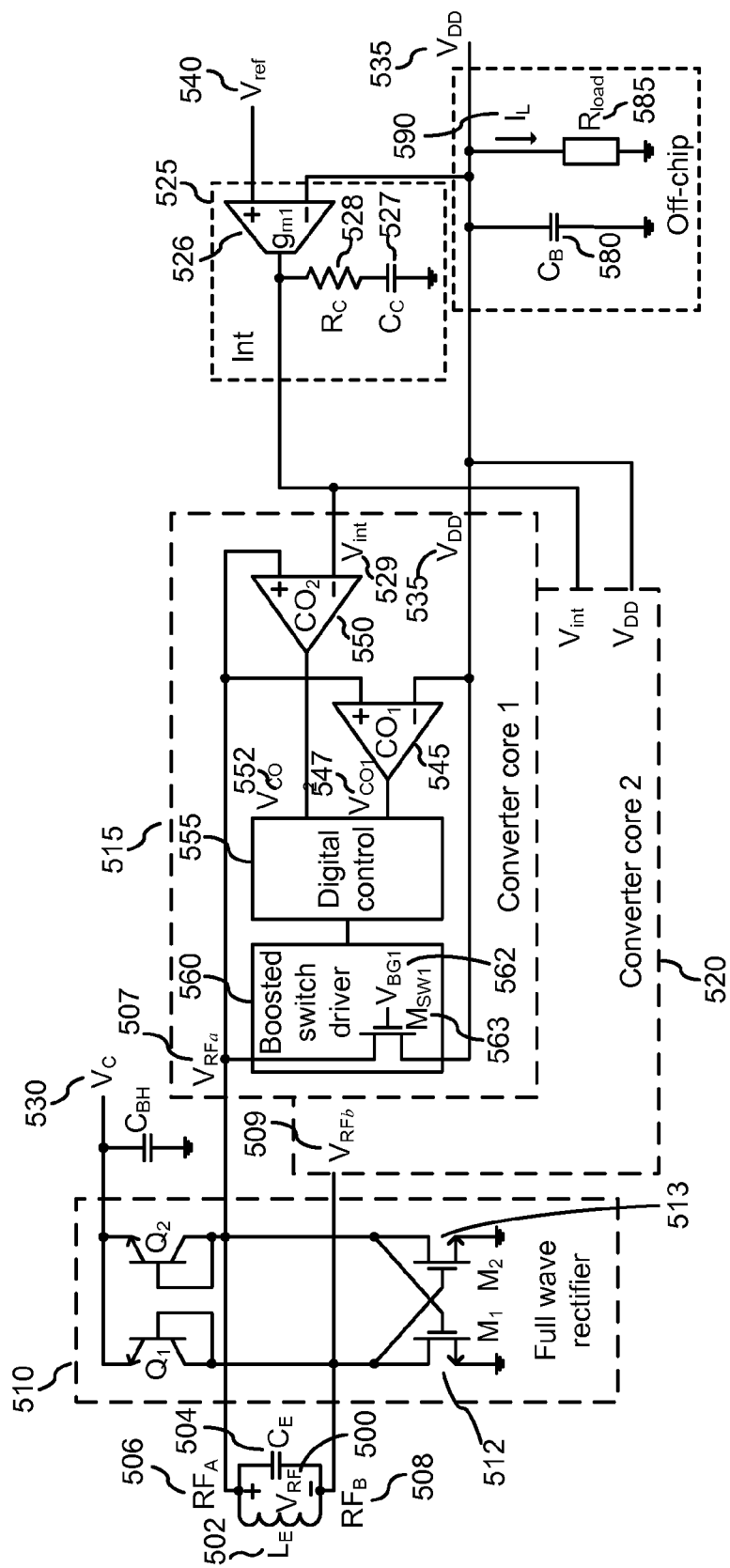
FIG. 5 shows a detailed block diagram of the converter of FIG. 4.

Referring now to FIG. 5 there is shown an embodiment of the converter that incorporates the timing controlled rectifier (200) shown in FIG. 4. A bypass capacitor $C_B$ (580) and a load $R_{load}$ (585) are off-chip components and thus are not part of the converter.

The converter unit in FIG. 5 is inductively powered from an external magnetic source (not shown). The external magnetic source induces a voltage $V_{RF}$ (500) across receiving coil $L_E$ (502). Capacitor $C_E$ (504) and coil $L_E$ (502) form a parallel resonant circuit and the value of tuning capacitor $C_E$ (504) is selected to establish a circuit resonant frequency of $f_{in}$. The induced voltage $V_{RF}$ (500) comprises a first voltage rail $RF_A$ (506) corresponding to a first voltage $V_{RFa}$ (507) and a second voltage rail $RF_B$ (508) corresponding to a second voltage $V_{RFb}$ (509). The power management unit further comprises a full-wave rectifier (510), a first converter core (515), a second converter core (520), and integrator (525). The full-wave rectifier (510) generates a high supply voltage $V_C$ (530), which is generally used to supply voltage to the converter cores (515, 520) in the power management unit as well as analog circuits in implantable devices (not shown).

The timing controlled rectifier (200) in FIG. 4 comprises one of the converter cores (515, 520) and the integrator (525) shown in FIG. 5. The timing controlled rectifier (200) generates an output voltage $V_{DD}$ (535), which is generally used to power digital control circuits and communication circuits in implantable devices (not shown).

The first converter core (515) comprises a first comparator $CO_1$ (545), a second comparator $CO_2$ (550), a digital control unit (555), and a boosted switch driver (560). Note that the boosted switch driver (560), shown in FIG. 5, is equivalent to the combination of the switch driver (445) and the transistor $M_{SW}$ (405), shown in FIG. 4. The second converter core (520) comprises components, not shown in FIG. 5, similar to those in the first converter core (515). Specifically, the second converter core (520) also comprises its own first comparator, second comparator, digital control unit, and boosted switch driver. An implementation of the integrator (525) is shown in FIG. 5 and comprises a transconductance amplifier (526), a capacitor $C_C$ (527), and a resistor $R_C$ (528).

As previously described with reference to FIG. 4, basic functionality of the converter cores (515, 520), the integrator (525), the digital control unit (555), and the boosted switch driver (560), which form a feedback loop, is to set the average value of the output voltage $V_{DD}$ (535) equal to a constant reference voltage $V_{ref}$ (540).

The integrator (525) has as one input the preselected reference voltage $V_{ref}$ (540) and the output voltage $V_{DD}$ (535) as another input and provides as an output, a voltage $V_{int}$ (529) equal to the integral of the difference of $V_{ref}$ (540) and $V_{DD}$ (535). The first comparator $CO_1$ (545) has as one input $V_{RFa}$ (507) and as another input $V_{DD}$ (535) and provides as an output voltage $V_{CO1}$ (547), which is a function of the difference between $V_{RFa}$ (507) and $V_{DD}$ (535). In a similar fashion, the second comparator $CO_2$ (550) has as inputs $V_{RFa}$ (507) and $V_{int}$ (529) and provides $V_{CO2}$ (552) as its output. A more detailed description of the functionality of the converter cores (515, 520) and the integrator (525) is given with reference to both FIGS. 5 and 6.

Figure 6:
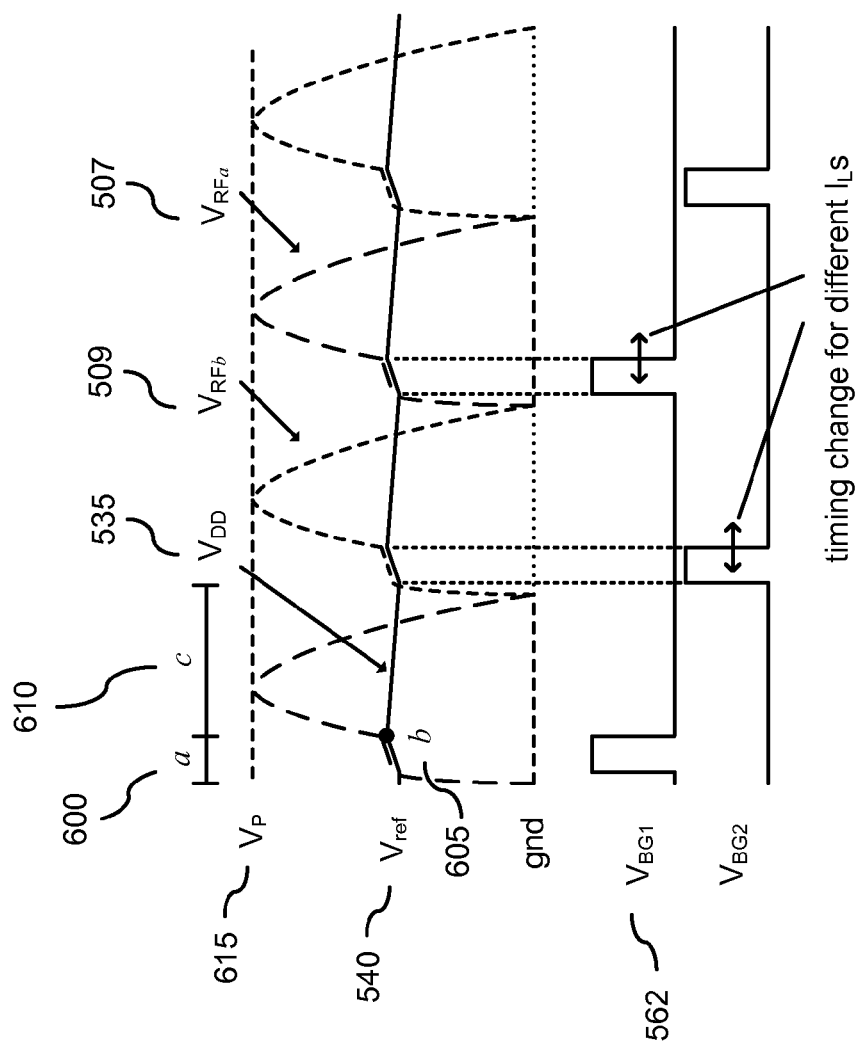
FIG. 6 shows voltage waveforms related to the operation of the timing controlled converter of FIG. 5.

As shown in FIG. 6, during a first time interval a (600), where the first voltage $V_{RFa}$ (507) is increasing, a first transistor $M_1$ (512) has the voltage $V_{RFa}$ (507) applied at its gate, the voltage $V_{RFb}$ (509) applied at its drain, and ground tied to its source. Since the gate voltage is sufficiently large during the time interval a (600), the second voltage rail $RF_B$ (508) is tied to the ground terminal. Consequently, the first transistor $M_1$ (512) is switched on and the second voltage rail $RF_B$ (508) is tied to ground.

When the voltage $V_{RFa}$ (507) becomes greater than the output voltage $V_{DD}$ (535), the first comparator output voltage $V_{CO1}$ (547) of the first comparator $CO_1$ (545) is set to high. When the voltage $V_{CO1}$ (547) is high, the digital control unit (555) sets a gate drive voltage $V_{BG1}$ (562) in the boosted switch driver (560) to high. When the gate drive voltage $V_{BG1}$ (562) is high, a transistor $M_{SW1}$ (563) is turned on, allowing current to flow from the first voltage rail $RF_A$ (506) to the bypass capacitor $C_B$ (580) and the load $R_{load}$ (585). As the result of an equivalent finite impedance attributable to the power receiving coil $L_E$ (502) and the tuning capacitor $C_E$ (504), the voltage $V_{RFa}$ (507) will be distorted as shown in FIG. 6. As previously mentioned, the feedback loop comprising the converter cores (515, 520), the integrator (525), the digital control unit (555), and the boosted switch driver (560) is utilized to set the average value of the output voltage $V_{DD}$ (535) equal to the constant reference voltage $V_{ref}$ (540).

The integrator (525) integrates the average difference between the constant reference voltage $V_{ref}$ (540) and the output voltage $V_{DD}$ (535). The integrator (525) outputs an integrator output voltage $V_{int}$ (529), which serves as a threshold value for the second comparator $CO_2$ (550). When the voltage $V_{RFa}$ (507) becomes greater than the voltage $V_{int}$ (529), such as at point b (605), the second comparator output voltage $V_{CO2}$ (552) is set to high. When the voltage $V_{CO2}$ (552) is high, the digital control unit (555) sets the gate drive voltage $V_{BG1}$ (562) to low and thus turns off the transistor $M_{SW1}$ (563). Current flow will cease for a time interval c (610) so that the amount of current delivered to the load $R_{load}$ (585) will keep the average value for the output voltage $V_{DD}$ (535) equal to the constant reference voltage $V_{ref}$ (540). Consequently, duration of time when transistor $M_{SW1}$ (563) is turned off depends on a load current $I_L$ (590).

To prevent current from flowing back from the output voltage $V_{DD}$ (535) to the first voltage rail $RF_A$ (506), transistor $M_{SW1}$ (563) is turned off before the voltage $V_{RFa}$ (507) reaches a peak value $V_P$ (615), as shown in FIG. 6. Current flowing from the output voltage $V_{DD}$ (535) to the first voltage rail $V_{RFa}$ (506) would cause the converter to lose regulation and reduce power efficiency η. High values for power efficiency η are obtained if the transistor $M_{SW1}$ (563) turns on when the voltage $V_{RFa}$ (507) is nearly equal to the voltage $V_{DD}$ (535).

One method to prevent current from flowing back from the output voltage $V_{DD}$ (535) to the first voltage rail $RF_A$ (506) requires design of the digital control unit (555) such that transistor $M_{SW1}$ (563) will not turn on when the voltage $V_{RFa}$ (507) decreases from its peak value $V_P$ (615). As seen in FIG. 6, the bias voltage $V_{BG1}$ (562) is set to low and thus transistor $M_{SW1}$ (563), is turned off for the time that the voltage $V_{RFa}$ (507) is decreasing from its peak value $V_P$ (615).

It should be noted that in FIG. 5 the second converter core (520) is illustrated by a black box for increased clarity. According to several embodiments of the invention, the second converter core (520) comprises a first comparator, second comparator, digital control unit, and boosted switch driver that parallel those used to implement the first converter core (515). The components of the second converter core (520) are not shown in FIG. 6. When the induced voltage $V_{RF}$ (500) enters a second half of its cycle, specifically the cycle where the voltage $V_{RFb}$ (509) starts increasing, the first voltage rail $RF_A$ (506) is switched to ground by the second transistor $M_2$ (513). Consequently, operation similar to that described for the time periods a (600) and c (610) will occur, except operation will involve the second converter core (520) as opposed to the first converter core (515).

Figures 7A, 7B:
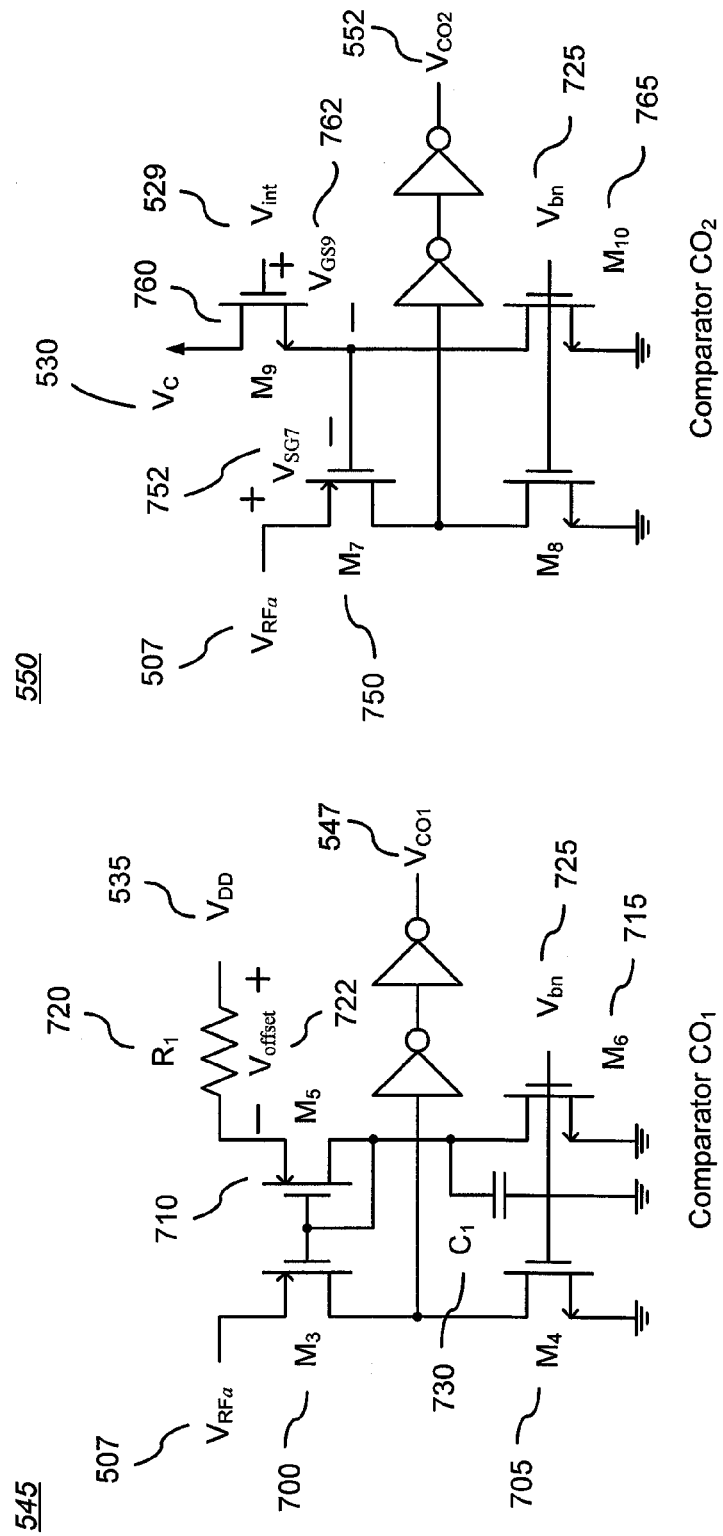
FIGS. 7A and 7B show first and second comparators, respectively, used in an implementation of the timing controlled converter of FIG. 4.

FIGS. 7A and 7B show a possible implementation of the first comparator $CO_1$ (545) and the second comparator $CO_2$ (550), respectively. The implementations of the comparators (545, 550) are based on an exemplary common-source amplifier topology. FIG. 7A shows one possible implementation of the first comparator $CO_1$ (545) shown in FIG. 5. The voltages $V_{RFa}$ (507), $V_{DD}$ (535), and $V_{CO2}$ (552) shown in FIG. 7B refer to the same voltages $V_{RFa}$ (507), $V_{DD}$ (535), and $V_{CO2}$ (552) shown in FIG. 5 and are thus given the same reference numerals in both figures. The first comparator $CO_1$ (545) has the voltages $V_{RFa}$ (507) and $V_{DD}$ (535) as its inputs and provides the voltage $V_{CO1}$ (547) as its output. The first comparator (545) compares the first voltage $V_{RFa}$ (507) and the output voltage $V_{DD}$ (535). In a first case where the voltage $V_{RFa}$ (507) becomes greater than the voltage $V_{DD}$ (535), a third transistor $M_3$ (700) turns on and comparator output voltage $V_{CO1}$ (552) is high. In a second case where the voltage $V_{RFa}$ (507) is less than the voltage $V_{DD}$ (535), the third transistor $M_3$ (700) turns off and the comparator output voltage $V_{CO1}$ (547) is low.

To maximize power efficiency q, the voltage $V_{CO1}$ (547) should be high when the voltage $V_{RFa}$ (507) is just slightly larger than the voltage $V_{DD}$ (535). One method to achieve this is by minimizing delay attributable to the first comparator $CO_1$ (545). To minimize delays due to the first comparator $CO_1$ (545), a resistor $R_1$ (720) is used in comparator $CO_1$ (545). The resistor $R_1$ (720) introduces a small offset voltage $V_{offset}$ (722). As a result of the small offset voltage $V_{offset}$ (722), the comparator output voltage $V_{CO1}$ (547) starts to turn high when the voltage $V_{RFa}$ (507) is just slightly larger than the voltage $V_{DD}$ (535) minus the offset voltage $V_{offset}$ (737). The first comparator $CO_1$ (545) sets the voltage $V_{CO1}$ (547) to high earlier than it would have set the voltage $V_{CO1}$ (547) to high had there been no offset voltage $V_{offset}$ (722). The earlier time at which the voltage $V_{CO1}$ (547) is set to high compensates for any delay attributable to the first comparator $CO_1$ (545).

For a given bias voltage $V_{bn}$ (725) set on a fourth transistor $M_4$ (705) and a sixth transistor $M_6$ (715), the resistance of the resistor $R_1$ (720) is optimized for a frequency of 1 MHz for $f_{in}$. A capacitor $C_1$ (730) is used to minimize fluctuations on the gate of transistor $M_3$ due to coupling between the output voltage $V_{DD}$ (535) and the voltage $V_{RFa}$ (507) through a parasitic capacitance $C_{GS3}$ (not shown) that exists between the gate and source of the third transistor $M_3$ (700).

FIG. 7B shows one possible implementation of the second comparator $CO_2$ (550) shown in FIG. 5. The voltages $V_{RFa}$ (507), $V_{int}$ (529), and $V_{CO1}$ (547) shown in FIG. 7B refer to the same voltages $V_{RFa}$ (507), $V_{int}$ (529), and $V_{CO1}$ (547) shown in FIG. 5 and are thus given the same reference numerals in both figures.

The second comparator $CO_2$ (550) has as inputs $V_{RFa}$ (507) and $V_{int}$ (529) and $V_{CO2}$ (552) as its output. The second comparator $CO_2$ (550) compares the values of $V_{RFa}$ (507) and $V_{int}$ (529) and in a first case where the voltage $V_{RFa}$ (507) exceeds the voltage $V_{int}$ (529), transistor $M_7$ (750) turns on and comparator output voltage $V_{CO2}$ (552) is high. Conversely, in a second case where $V_{int}$ (529) exceeds $V_{RFa}$ (507), transistor $M_7$ (750) turns off and comparator output voltage $V_{CO2}$ (552) is low.

An exemplary source follower configuration, comprising transistor $M_9$ (760) and transistor $M_{10}$ (765), is used for its voltage buffering characteristic. Specifically, the source follower configuration buffers the integrator output voltage $V_{int}$ (529) from anomalies due to coupling between the voltage $V_{RFa}$ (507) and the voltage $V_{int}$ (529) through a parasitic capacitance $C_{GS7}$ (not shown) that exists between gate and source of transistor $M_7$ (750).

Any voltage offsets effecting $V_{RFa}$ (507) and $V_{int}$ (529) due to a source to gate voltage $V_{SG7}$ (752) of $M_7$ (750) and a gate to source voltage $V_{GS9}$ (762) of transistor $M_9$ (760) is automatically compensated for by way of the feedback loop. As noted earlier in relation to FIG. 5, the feedback loop comprises the integrator (525), comparators (545, 550), digital control unit (555), and boosted switch driver (560). The feedback loop will adjust the voltage $V_{int}$ (529) to compensate for any comparator offsets due to the voltages $V_{SG7}$ (752) and $V_{GS9}$ (762). Since the voltage $V_{int}$ (529) is the output of the integrator (525), as shown in FIG. 5, the value of the output voltage $V_{DD}$ (535) is influenced by any offset voltages attributable to transconductance amplifier (526).

As previously mentioned with regard to FIGS. 5, 7A, and 7B, in order to obtain a high power efficiency η, the output voltage $V_{DD}$ (535) is driven close to the voltage $V_{RFa}$ (507) by the transistor $M_{SW1}$ (563) and the gate drive voltage $V_{BG1}$ (562). Similarly, the output voltage $V_{DD}$ (535) is driven close to the voltage $V_{RFb}$ (509) by a transistor $M_{SW2}$ and a gate drive voltage $V_{BG2}$. The transistor $M_{SW2}$ and gate drive voltage $V_{BG2}$ are not directly shown in FIG. 5. They are implicitly found in the second converter core (520), and the transistor $M_{SW2}$ and gate drive voltage $V_{BG2}$ parallel the transistor $M_{SW1}$ (563) and the gate drive voltage $V_{BG1}$ (562), respectively, of the first converter core (515). Hence, the transistors $M_{SW1}$ (563) and $M_{SW2}$ are generally designed to have low on-resistance which can be accomplished by increasing gate drive voltages $V_{BG1}$ (562) and $V_{BG2}$ (not shown) of the transistors $M_{SW1}$ (563) and $M_{SW2}$ (not shown), respectively.

Figure 8:
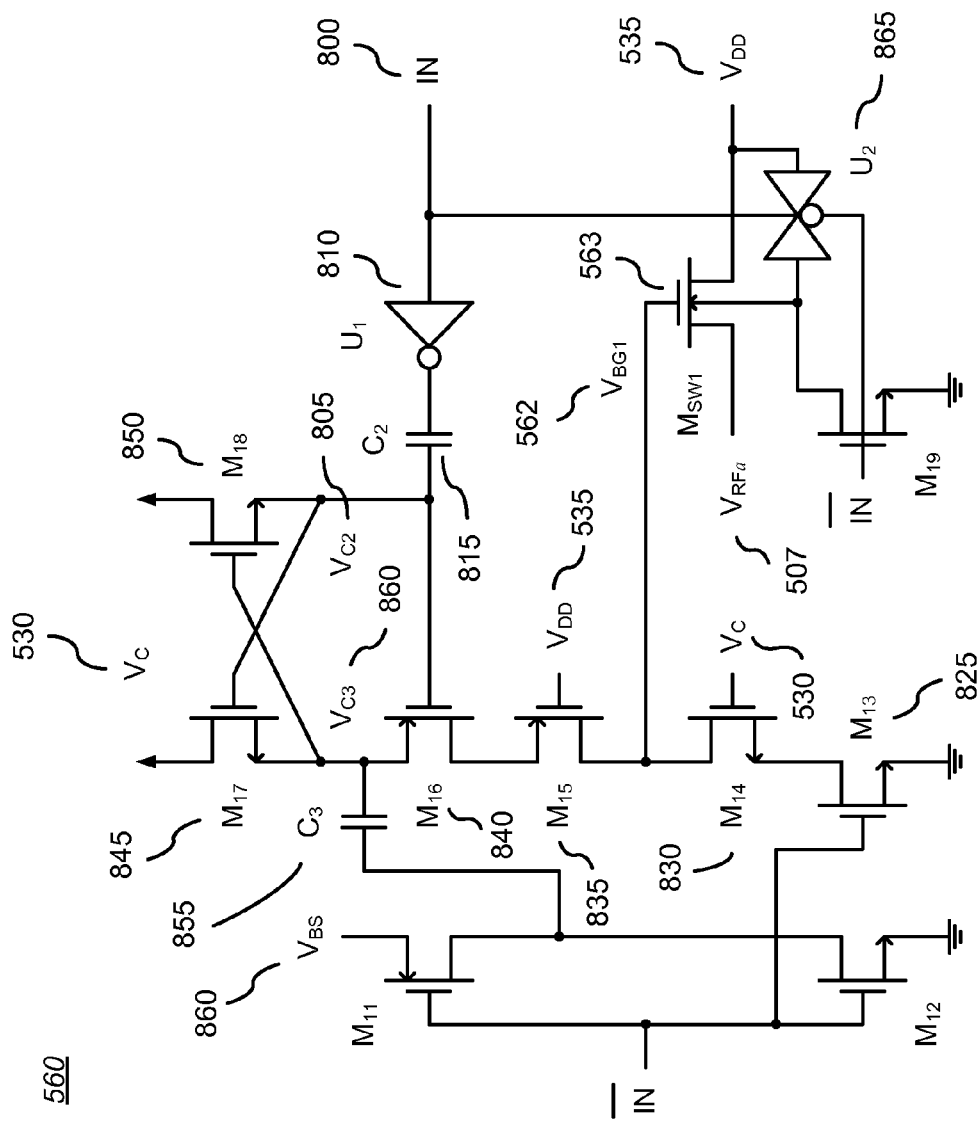
FIG. 8 shows an implementation of a boosted switch driver that is used in an implementation of the timing controlled converter of FIG. 4.

FIG. 8 shows an implementation of the boosted switch driver (560) shown in FIG. 5. Specifically, the boosted switch driver (560) is used for generating a large value for the gate drive voltage $V_{BG1}$ (562). The voltages $V_{RFa}$ (507), $V_{DD}$ (535), $V_C$ (530), and $V_{BG1}$ (562) shown in FIG. 8 refer to the same voltages $V_{RFa}$ (507), $V_{DD}$ (535), $V_C$ (530), and $V_{BG1}$ (562) shown in FIG. 5 and are thus given the same reference numerals in both figures. Similarly, the transistor $M_{SW1}$ (563) shown in FIG. 8 refers to the same transistor $M_{SW1}$ (563) shown in FIG. 5 and is thus given the same reference numeral in both figures.

When a driver input 'IN' (800) (same as the output of the digital control (555) shown in FIG. 5) is low, capacitor voltage $V_{C2}$ (805) is driven to a high voltage by a first inverter $U_1$ (810) through capacitor $C_2$ (815). The voltage $V_{C2}$ (805) is applied to the gate of transistor $M_{16}$ (840) and transistor $M_{17}$ (845), and the source of transistor $M_{18}$ (850). When the voltage $V_{C2}$ (805) is high, transistor $M_{17}$ (845) is turned on due to the high gate voltage applied to transistor $M_{17}$ (845) and transistor $M_{18}$ (850) is turned off due to the high source voltage applied to transistor $M_{18}$ (850). As a result, the high supply voltage $V_C$ (530) is applied to capacitor $C_3$ (855), charging capacitor $C_3$ (855) such that capacitor voltage $V_{C3}$ (860) is close to the high supply voltage $V_C$ (530). The gate drive voltage $V_{BG1}$ (562) is driven to ground through transistor $M_{14}$ (830) and transistor $M_{13}$ (825).

When the driver input 'IN' (800) is high, capacitor voltage $V_{C2}$ (805) will switch to a low value. Transistor $M_{17}$ (845) is turned off due to the low value of $V_{C2}$ (805) applied at its gate. Transistor $M_{18}$ (850) is turned on due to the low value of $V_{C2}$ (805) applied at its source. As a result of transistor $M_{18}$ (850) turning on, the high supply voltage $V_C$ (530) is applied to capacitor $C_2$ (815), charging capacitor $C_2$ (815) such that capacitor voltage $V_{C2}$ (805) is close to the high supply voltage $V_C$ (530). Additionally, both capacitor voltage $V_{C3}$ (860) and the gate drive voltage $V_{BG1}$ (562) will be driven to a voltage $(V_{BS}+V_C)C_3/(C_3+C_{G\_SW1})$ where $C_{G\_SW1}$ is a total gate capacitance of transistor $M_{SW1}$ (563) plus other parasitic capacitances. Consequently, a large value for the gate drive voltage $V_{BG1}$ (562) can be obtained when the capacitance of capacitor $C_3$ (855) is much larger than $C_{G\_SW1}$.

To maximize the gate drive voltage $V_{BG1}$ (562), capacitor $C_3$ (855) is implemented using both MIM capacitors and MOS capacitors. Although either the high supply voltage $V_C$ (530) or the output voltage $V_{DD}$ (535) can be used in place of a bias voltage $V_{BS}$ (862), power efficiency q is found to be slightly higher when the voltage $V_{DD}$ (535) is used. Transistors $M_{14}$ (830) and $M_{15}$ (835) are used for reducing the drain-to-gate voltage on transistors $M_{13}$ (825) and $M_{16}$ (840), respectively.

Since a deep NWell process can be used, transistor $M_{SW1}$ (563) is connected to the voltage $V_{DD}$ (535) through the transmission gate $U_2$ (865) to reduce body effect. As a result of reducing the body effect, the on-resistance of the transistor $M_{SW1}$ (563) is also reduced.

A number of embodiments of the invention have been disclosed. Nevertheless, it will be understood that various modifications may be made without departing from the spirit and scope of the present disclosure. For example, the integrator 415 as configured, takes the form of a proportional control circuit that provides a proportional control signal as a function of the difference between the output voltage $V_{DD}$ (102) and the preselected reference voltage. Other types of proportional control circuits are also contemplated by the present invention such as for example, but certainly not limited to, a circuit commonly known as a "bang-bang" controller circuit. Accordingly, other embodiments including circuits configured as proportional control circuits are also within the scope of the following claims.

What is claimed is:

1. A method for supplying a regulated output voltage to a load circuit, utilizing a converter circuit configured to switchably couple a time varying input signal to the load circuit, the method comprising the steps of:
    integrating the difference between the regulated output voltage and a preselected reference voltage to thereby provide a control signal; and
    switchably coupling the time varying input signal to the load circuit for controlled periods of time when the polarity of the regulated output voltage and the polarity of the time varying signal are the same, said controlled period of time:
        commencing when the absolute value of the time varying signal becomes greater than the absolute value of the regulated output voltage; and
        terminating when the absolute value of the time varying input signal becomes greater than the absolute value of the control signal for maintaining the average value of the regulated output voltage equal to the preselected reference voltage.

2. The method of claim 1 further comprising the step of providing a first voltage being a function of the difference between the time varying input signal and the control signal.

3. The method of claim 2 further comprising the step of providing a second voltage being a function of the difference between the time varying input signal and the output voltage.

4. The method of claim 3 further comprising the steps of providing a first drive signal when the second voltage indicates that the absolute value of the time varying signal becomes greater than the absolute value of the output voltage and further providing a second drive signal when the first voltage indicates that the absolute value of the time varying signal becomes greater than the absolute value of the control signal.

5. The method of claim 4 further comprising the steps of coupling the time varying input signal to the load circuit upon occurrence of the first drive signal and decoupling the time varying input signal from the load circuit upon the occurrence of the second drive signal.

6. A method of supplying a regulated output voltage to a load circuit, said method utilizing a converter circuit configured to switchably couple a time varying input signal to the load circuit for providing a regulated output voltage having an average value equal to a preselected reference voltage, said method comprising the steps of:
    providing a proportional control signal as a function of the difference between the regulated output voltage and the preselected reference voltage for providing the proportional control signal; and
    switchably coupling the time varying input signal to the load circuit for controlled periods of time, said controlled period of time:
        commencing when the absolute value of the time varying signal becomes greater than the absolute value of the output voltage; and
        terminating when the absolute value of the time varying input signal becomes greater than the absolute value of the control signal, for thereby maintaining the average value of the output voltage equal to the preselected reference voltage.

* * * * *